(12) United States Patent
Hamill et al.

(10) Patent No.: US 9,458,148 B2
(45) Date of Patent: Oct. 4, 2016

(54) CRYSTALLINE FORM OF MASITINIB

(71) Applicant: SANDOZ AG, Basel (CH)

(72) Inventors: Noel Hamill, Craigavon (GB); Lorraine Donaghy, Craigavon (GB)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/573,597

(22) Filed: Dec. 17, 2014

(65) Prior Publication Data

US 2015/0166524 A1   Jun. 18, 2015

(30) Foreign Application Priority Data

Dec. 18, 2013 (EP) .................................... 13198012

(51) Int. Cl.
*C07D 417/04* (2006.01)
*A61K 31/496* (2006.01)

(52) U.S. Cl.
CPC .................................. *C07D 417/04* (2013.01)

(58) Field of Classification Search
None
See application file for complete search history.

(56) References Cited

U.S. PATENT DOCUMENTS 8,492,545 B2   7/2013   Moussy et al.

FOREIGN PATENT DOCUMENTS

| WO | 2004/014903 | 2/2004 |
|----|-------------|--------|
| WO | 2008/098949 | 8/2008 |

OTHER PUBLICATIONS

European Search Report issued in European Patent Application No. 13198012.0-1462, Feb. 18, 2014, pp. 1-8.

*Primary Examiner* — Emily Bernhardt
(74) *Attorney, Agent, or Firm* — Jeffrey S. Melcher; Manelli Selter PLLC

(57) ABSTRACT

Provided is a polymorphic form of Masitinib mesylate, processes for its preparation, compositions comprising it and their medical use.

10 Claims, 3 Drawing Sheets

CRYSTALLINE FORM OF MASITINIB

This applications claims priority under 35 U.S.C. 119(a) to European application No. 13198012.0 filed before the European Patent Office on 18 Dec. 2013, the complete disclosure of which is incorporated herein by reference.

FIELD OF INDUSTRIAL APPLICABILITY

The present invention relates to a polymorphic form of Masitinib mesylate, processes for its preparation, compositions comprising it and their medical use.

BACKGROUND OF THE DISCLOSURE

Masitinib is a c-kit inhibitor for the potential treatment of cancer (gastrointestinal stromal tumor (GIST), pancreatic cancer, multiple myeloma (MM), metastatic melanoma), inflammatory diseases (mastocytosis, rheumatoid arthritis (RA) and asthma), and CNS disorders (Alzheimer's disease (AD), multiple sclerosis (MS)) in human subjects. It is already approved as a veterinary medicine for the treatment of mast cell tumors. Masitinib is disclosed in WO 2004/014903 A2.

WO 2008/098949 A1 discloses a crystalline form of Masitinib mesylate, hereinafter called crystal form I, characterized by an X-ray diffraction pattern. The positions of the XPRD peaks are disclosed on page 23. It is also disclosed that the form remains dry at 80% relative humidity and thermodynamically stable at temperatures below 200° C.

In the file history of European patent application 11170200.7, applicant's response to the eESR dated Mar. 20, 2012, (hereinunder called "response to the eESR"), two more polymorphic forms of masitinib mesylate are mentioned and named DRX2 and DRX3. DRX2 is described to be a likely hemihydrate which is stable only at 25° C. and which slowly, but fully, converts to DRX1, the polymorph disclosed in WO2008/098949, upon temperature increase. The conversion is described to be even faster in conditions that lower the activation energy barrier. DRX3 is described as an anhydrous form, which is stable under dry conditions only and which otherwise quickly converts to DRX2. It is concluded that DRX1 be the "ideal" candidate for developing a pharmaceutical dosage form, even though it is recognized that DRX1 is mildly hygroscopic.

As DRX1 presently appears to be the only available polymorph suitable for pharmaceutical development, there remains thus a need for a further polymorph of masitinib mesylate suitable for the development of pharmaceutical dosage forms, preferably one with improved properties. Moreover, as hygroscopic solid forms pose a limitation to the types of pharmaceutical dosage forms which can be prepared from them, for the types of excipients which can be used in combination with them and for the conditions and processes, which can be employed during the preparation of a pharmaceutical dosage form comprising a hygroscopic solid form of masitinib mesylate, there is thus a need for a solid form of masitinib mesylate, which is non-hygroscopic at a range of relative humidity which is typical of the regular working conditions encountered during finished dosage form preparation, and which is stable also at temperatures above 25° C.

SUMMARY OF THE DISCLOSURE

The present disclosure provides a new crystalline form of Masitinib mesylate, which is herein called form H, and a process for its preparation. Form H can be obtained in high polymorphic purity and it can be used in the manufacture of pharmaceutical dosage forms comprising masitinib mesylate.

DETAILED DESCRIPTION OF THE DISCLOSURE

The disclosure relates to a crystalline form of Masitinib mesylate, which is described and characterized herein in more detail.

Definitions

As used herein "polymorph" refers to crystalline forms having the same chemical composition but different spatial arrangements of the molecules, atoms, and/or ions forming the crystal.

As used herein "hydrate" refers to a crystalline form of a molecule that further comprises molecules of water incorporated into the crystalline lattice structure. The water molecules in the hydrate may be present in a regular arrangement and/or a non-ordered arrangement. The hydrate may comprise either a stoichiometric or nonstoichiometric amount of the water molecules. For example, a hydrate with a nonstoichiometric amount of water molecules may result from partial loss of water from the stoichiometric hydrate. Hydrates may occur as dimers or oligomers comprising more than one molecule of Masitinib within the crystalline lattice structure.

As used herein "amorphous" refers to a solid form of a molecule that is not crystalline. An amorphous solid does not display a definite X-ray diffraction pattern.

As used herein, the term "substantially pure" with reference to a particular polymorphic form means that the polymorphic form includes less than 10%, preferably less than 5%, more preferably less than 3%, most preferably less than 1% by weight of any other physical forms of the compound.

As used herein 'aspect ratio' refers to the ratio of the length of the crystals (L) over the width (W). The aspect ratio (A) is therefore defined as: A=L/W. The dimensions of a crystal can be measured using an optical microscope. Typical measurement accuracy is +/−30%

Crystal Form H

Figure 1:
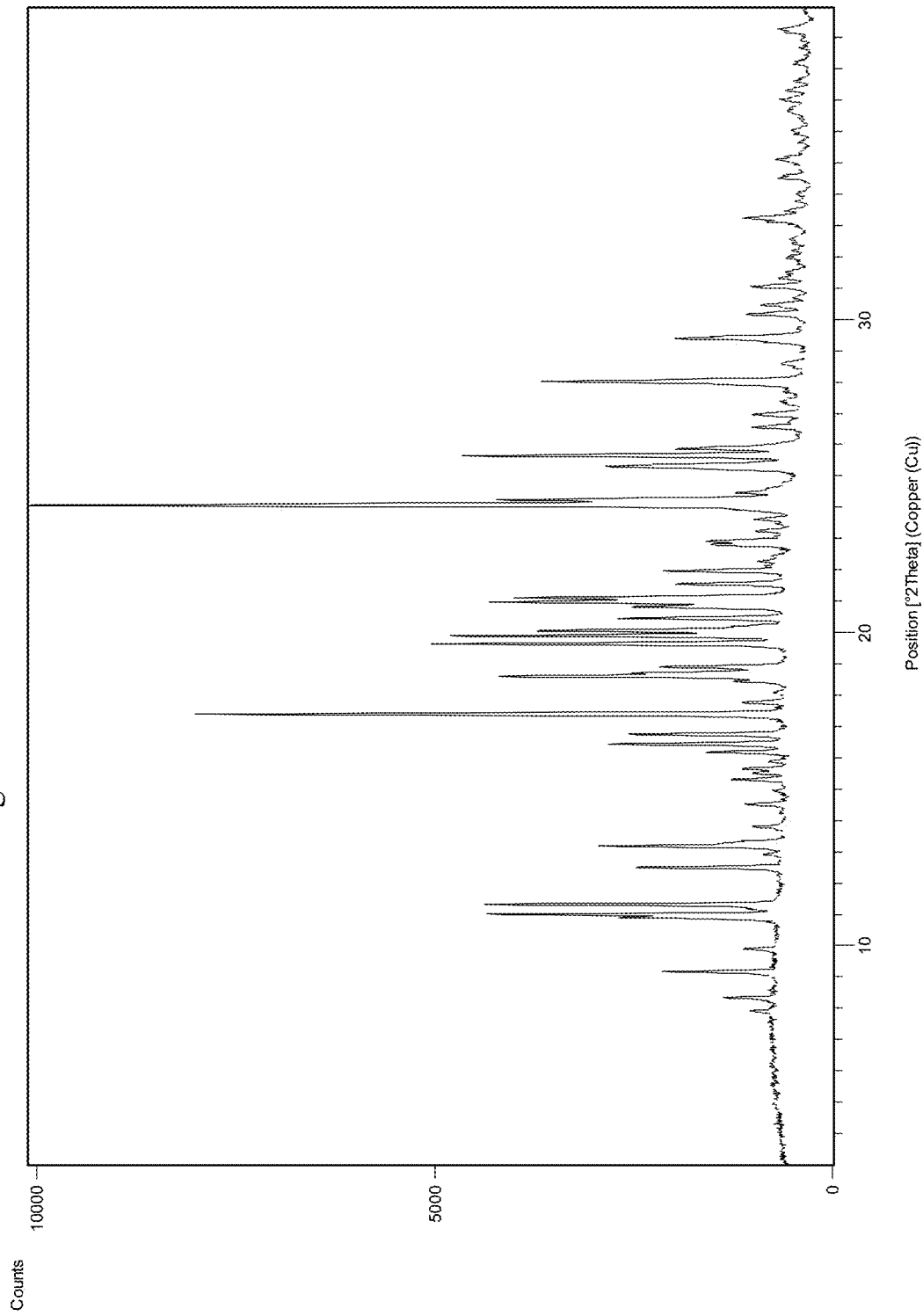
FIG. 1 illustrates the x-ray powder diffraction patterns of crystalline form H of Masitinib.
Figure 2:
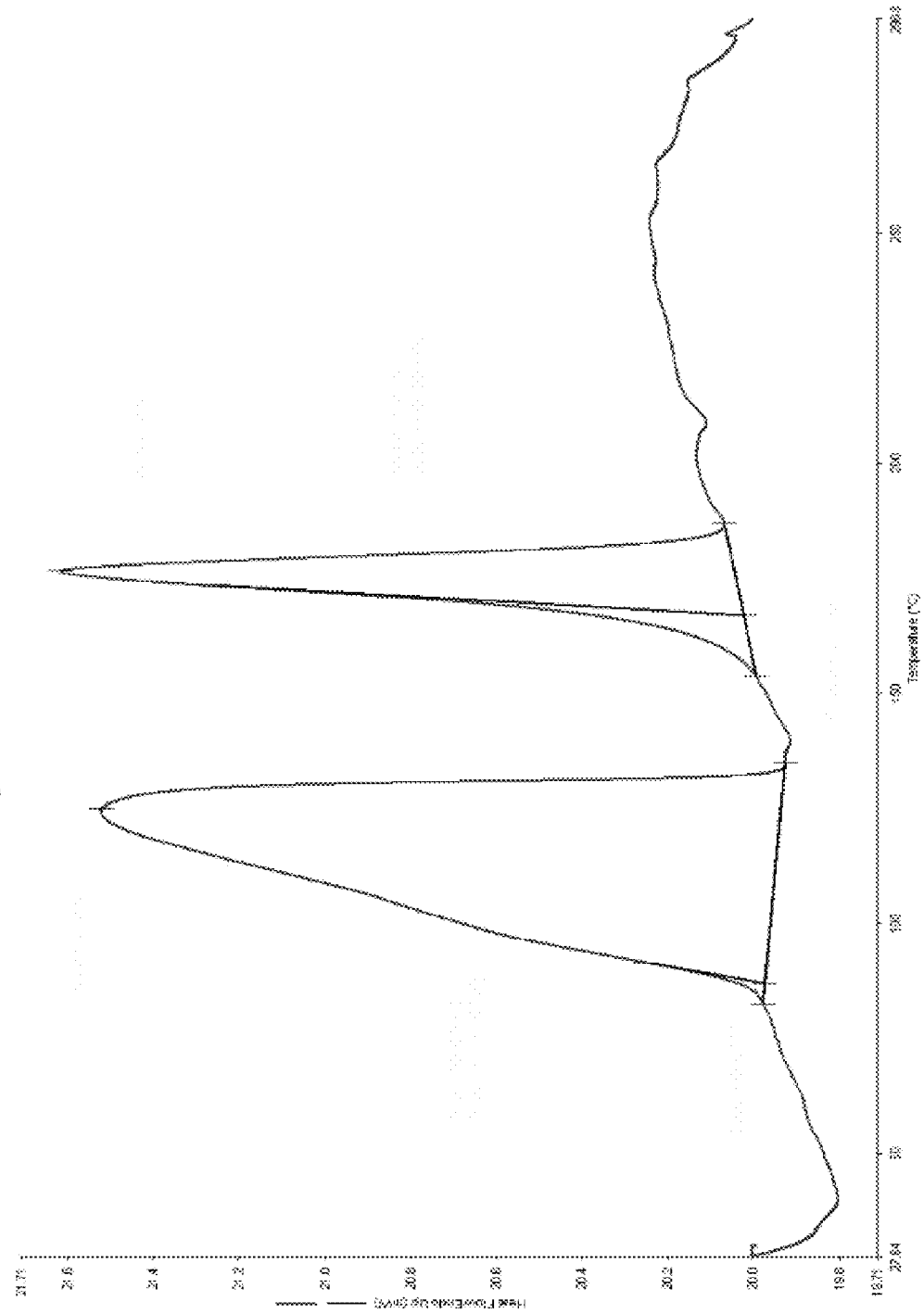
FIG. 2 illustrates a DSC trace of crystalline Form H. The X-axis shows temperature in ° C.; the Y-axis shows heat flow in mW.
Figure 3:
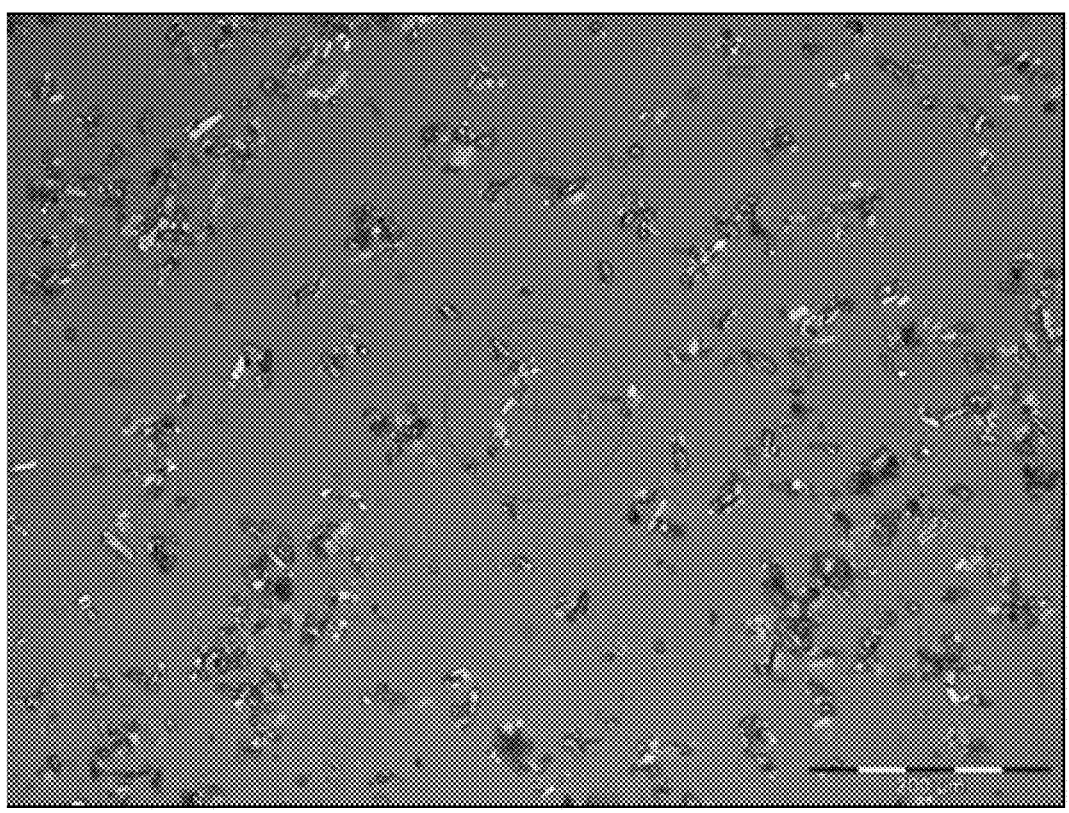
FIG. 3 illustrates the appearance of crystalline form H of Masitinib under polarized light microscopy.

The present invention provides a crystalline form of Masitinib mesylate having an X-ray diffraction spectrum comprising the peaks as mentioned in claim 1, for example a crystalline form of Masitinib mesylate having an X-ray diffraction spectrum substantially the same as the X-ray powder diffraction spectrum shown in FIG. 1.

The term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Consequently, it is to be understood that the crystal form of the present invention is not limited to the crystal form that provides X-ray diffraction patterns completely identical to the X-ray diffraction patterns depicted in the accompanying figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art. In one embodiment of the present invention, crystalline form H of masitinib mesylate is provided in substantially pure form.

Crystalline form H of masitinib mesylate is a hydrate, i.e. it may include from 2.0% to 7.0% of water, preferably from 3.0% to 6.0% of water, more preferably from 3.0% to 5.0% of water (w/w), in particular at room temperature and at 40% r.h. It may also contain solvents other than water, which solvents were used during its preparation, preferably from 0% to 5 mol %, such as from 0.001% to 1.0%. Water and solvent content can be determined by thermogravimetric analysis and the skilled person will understand to distinguish between the two, if necessary, using additional techniques, such as NMR.

Crystalline form H may be characterized by a x-ray powder diffraction pattern (XRPD) comprising peaks at 2θ values of 7.8, 8.3, 10.9, 11.3, 24.0, and 33.2, measured at a temperature of about 20° C. and an x-ray wavelength (CuKα), λ, of 1.5418 Å. Preferably, crystalline form H form may be characterized by an x-ray powder diffraction pattern comprising 2θ values of 7.8, 8.3, 10.9, 11.0, 11.3, 17.4, 24.0, 28.0 and 33.2, measured at a temperature of about 20° C. and an x-ray wavelength (CuKα), λ, of 1.5418 Å. A listing of peaks with a relative intensity above 5%, their heights and relative intensities are reported in the following table:

| Pos. [°2Th.] | Rel. Int. [%] |
| --- | --- |
| 7.8914 | 5.48 |
| 8.3235 | 7.14 |
| 9.161 | 15.61 |
| 9.1838 | 7.81 |
| 9.8827 | 5.14 |
| 10.8937 | 30.35 |
| 10.9208 | 15.17 |
| 10.992 | 30.05 |
| 11.0194 | 15.03 |
| 11.3077 | 40.2 |
| 11.3359 | 20.1 |
| 12.4898 | 20.15 |
| 12.5209 | 10.08 |
| 13.1665 | 27.01 |
| 13.1993 | 13.51 |
| 13.2884 | 10.49 |
| 13.3215 | 5.24 |
| 14.5014 | 5.88 |
| 15.2937 | 7.93 |
| 15.639 | 5.56 |
| 16.1688 | 9.73 |
| 16.4262 | 23.61 |
| 16.4673 | 11.8 |
| 16.7379 | 22.05 |
| 16.7797 | 11.02 |
| 17.381 | 75.95 |
| 17.4245 | 37.97 |
| 17.7553 | 5.98 |
| 18.4268 | 7.34 |
| 18.5908 | 39.54 |
| 18.6374 | 19.77 |
| 18.7043 | 18.73 |
| 18.7512 | 9.37 |
| 18.8884 | 19.5 |
| 18.9358 | 9.75 |
| 19.6261 | 46.66 |
| 19.6753 | 23.33 |
| 19.883 | 40.95 |
| 19.9329 | 20.47 |
| 20.0488 | 41.66 |
| 20.0991 | 20.83 |
| 20.443 | 20.15 |
| 20.4943 | 10.07 |
| 20.808 | 25.31 |
| 20.8603 | 12.65 |
| 20.9646 | 41.57 |
| 21.0173 | 20.78 |
| 21.0983 | 38.05 |
| 21.1513 | 19.02 |
| 21.538 | 15.92 |
| 21.5921 | 7.96 |
| 21.955 | 16.27 |
| 22.0102 | 8.14 |
| 22.7946 | 13.28 |
| 22.852 | 6.64 |
| 22.9149 | 10.75 |
| 22.9727 | 5.37 |
| 24.0555 | 100 |
| 24.1162 | 50 |
| 24.2268 | 40.49 |
| 24.2879 | 20.24 |
| 24.4444 | 20.95 |
| 24.5061 | 10.47 |
| 25.2916 | 47.3 |
| 25.3555 | 23.65 |
| 25.6357 | 46.22 |
| 25.7004 | 23.11 |
| 25.8662 | 19.45 |
| 25.9316 | 9.73 |
| 26.5458 | 6.13 |
| 26.9486 | 7.51 |
| 27.9182 | 14.44 |
| 27.9889 | 7.22 |
| 28.0119 | 35.98 |
| 28.0829 | 17.99 |
| 29.3877 | 22.29 |
| 29.4623 | 11.14 |
| 30.1515 | 9.49 |
| 30.4559 | 7.14 |
| 31.0339 | 8.27 |
| 33.2423 | 10.11 |
| 33.3273 | 5.06 |
| 34.7295 | 5.7 |
| 34.9575 | 5.44 |
| 35.1057 | 6.79 |
| 36.6494 | 10.5 |
| 36.7437 | 5.25 |
| 37.0008 | 5.99 |
| 39.2672 | 8.07 |

In a preferred embodiment, crystal form H is in substantially pure form. Preferably, Form H includes less than 5%, more preferably less than 3%, even more preferably less than 2%, most preferably less than 1% by weight of crystal form I.

Crystalline form I is characterized by a x-ray powder diffraction pattern (XRPD) comprising peaks at 2θ values of 11.04, 14.48, 16.72, 18.22 and 19.25, measured at a temperature of about 20° C. and an x-ray wavelength (CuKα), λ, of 1.5418 Å. Thus, pure crystalline form H of the present invention may preferably be characterized by an x-ray powder diffraction pattern comprising no significant peak at a 2θ value of 19.25, measured at a temperature of about 20° C. and an x-ray wavelength (CuKα), λ, of 1.5418 Å. A significant peak is defined as a peak with an average relative intensity of at least 3% of the most intense peak of an XRPD, (results from 10 independent measurements are averaged).

Alternatively, crystalline form H of masitinib mesylate may be characterized by the unit cell of the crystal. The present invention therefore also relates to crystalline masitinib mesylate characterized by a monoclinic crystal system of space group P1 21 1. The unit cell is preferably characterized by a cell volume of from 3785 $Å^3$ to 3800 $Å^3$, such as about 3793 $Å^3$, a value for the lattice constant a of 22.74+/−0.04 Å, for b of 8.68+/−0.04 Å, and for c of 20.65+/−0.04 Å.

The invention also relates to a composition comprising, and in particular consisting of, masitinib mesylate crystals, wherein the aspect ratio of the masitinib mesylate crystals is from 1 to 5, preferably from 1 to 3. Preferably the masitinib mesylate crystals are crystalline masitinib mesylate form H.

Preparation Process

In one method to prepare crystals, amorphous Masitinib mesylate is suspended and/or stirred in a mixture comprising water and dioxane or water and ethanol to obtain a slurry, which may be kept at room temperature for a time sufficient to allow formation of masitinib mesylate form H, such as 7 days, and then isolating crystalline form H of masitinib mesylate. The term "slurry", as used herein, means a saturated solution of the compound, which may also contain an additional amount of the compound to afford a heterogeneous mixture of the compound and a solvent at a given temperature.

A suitable solvent for the preparation of crystalline form H is a mixture comprising water and ethanol, such as water/ethanol azeotrope. A further suitable solvent for the preparation of crystalline form H is a mixture comprising water and dioxane.

The water content in the solvent mixture in the case of ethanol/water is preferably from 0.2% to 20%, more preferably from 0.5% to 10%, even more preferably from 1% to 8% by weight. The water content in the solvent mixture in the case of dioxane/water is preferably from 0.2% to 20%, more preferably from 0.5% to 10%, even more preferably from 1% to 8% by weight.

Seed crystals may be added to any crystallization mixture to promote crystallization. Seeding may be employed to control growth of a particular polymorph or to control the particle size distribution of the crystalline product. The crystallization mixture may be gently centrifuged or carefully filtered under vacuum to afford the desired crystalline form H. Crystalline form H may be prepared directly from the reaction medium of the final process for preparing masitinib mesylate. This may be achieved, for example, by employing in the final process step a solvent or a mixture of solvents from which masitinib mesylate form H may be crystallized.

Crystalline form H of masitinib mesylate can be preferably generated using one of the following methods.

Method A

A slurry is generated by suspending amorphous masitinib mesylate obtained by freeze drying in azeotropic ethanol at room temperature. The slurry is then kept at room temperature for 7 days. The resulting slurry is then filtered and the isolated solid gently air dried to provide the crystalline form of the present invention.

Method B

A slurry is generated by suspending amorphous masitinib mesylate obtained by freeze drying in dioxane at room temperature. The slurry is then kept at room temperature for 7 days. The resulting slurry is then filtered and the isolated solid gently air dried to provide the crystalline form of the present invention.

Advantages

Crystalline form H of masitinib mesylate provides several benefits over the known crystalline form I, since, with its favorable aspect ratio (see PLM picture of a sample in FIG. 4) it is less susceptible to mechanical manipulation, e.g. crystalline form H does not come in the form of needles which can change upon mechanical stress. Furthermore, crystal form H is less hygroscopic than form I. In an interval of relative humidity between 40% and 70% r.h. form H absorbs less than 0.5 weight % of water as determined in a DVS experiment. Moreover, and contrary to the hydrate mentioned in the eESR, it is a stable hydrated form which is suitable for development of a pharmaceutical dosage form. A further advantage of the beneficial aspect ratio of crystalline form H of masitinib mesylate is that this allows for improved processability of the crystal form of the present invention.

Medical Use and Formulations

The crystalline form of the invention may be used in the treatment of cancer (gastrointestinal stromal tumor (GIST), pancreatic cancer, multiple myeloma (MM) and metastatic melanoma), inflammatory diseases (mastocytosis, rheumatoid arthritis (RA) and asthma), and CNS disorders (Alzheimer's disease (AD), multiple sclerosis (MS)) in human subjects, and in the treatment of mastocytosis in dogs. It may be formulated with one or more excipients or other active pharmaceutical ingredients to provide formulations suitable for the treatment of the indications identified above. Such formulations may optionally include one or more other components selected, for example, from the group consisting of excipients, such as diluents, binders, disintegrants, lubricants, preservatives and coating materials, and other active pharmaceutical ingredients of different molecular structure.

Formulation example for film coated tablets: tablet cores are prepared from 500 mg masitinib mesylate crystal form H, microcrystalline cellulose, povidone K30, crospovidone and magnesium stearate. Tablet cores are then film coated.

X-Ray Powder Diffraction (XRPD)

XRPD analysis was carried out on a Panalytical Xpert Pro diffractometer, equipped with a Cu X-ray tube and a Pixcel detector system, scanning the samples between 3 and 40° 2θ. For small sample amounts, the material was gently compressed onto a glass slide, fitted into an XRPD sample holder.

| Raw Data Origin | Panalytical Xpert Pro |
|---|---|
| Start Position [°2Th.] | 3.0000 |
| End Position [°2Th.] | 40.000 |
| Step Size [°2Th.] | 0.0130 |
| *Scan Step Time [s] | 1 |
| Scan Type | Continuous |
| Offset [°2Th.] | 0.0000 |
| Divergence Slit Type | Fixed |
| Divergence Slit Size [°] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 (nominal) |
| Generator Settings | 40 mA, 40 kV |
| Diffractometer Type | d5000 |
| Goniometer Radius [mm] | 217.50 |
| Incident Beam Monochromator | No |
| Diffracted Beam Monochromator | (Graphite) |
| Spinning | No |

*Note: For some experiments, in order to improve the signal to noise ratio, the scan step time was increased to 5 or 12 seconds and/or a zero background slide was employed.

Polarised Light Microscopy (PLM)

The presence of birefringence was determined using an an Olympus BX51 using cross polarised light and a first order red compensator plate. The microscope was equipped with a Smiths IlluminatIR camera and SynchronizIR image capture software. All images were recorded using the 10× objective for routine analysis.

Dynamic Vapour Sorption (DVS)

Dynamic Vapour Sorption (DVS) was performed using a Hiden Analytical Instruments IGAsorp Vapour Sorption Balance. Approximately 30 mg of sample was placed into a wire-mesh vapour sorption balance pan, loaded into the IGAsorp vapour sorption balance and held at 25° C.±0.1° C. The sample was subjected to a step profile from 40% RH to 90% RH at 10% increments, followed by desorption from 90% RH to 0% RH at 10% increments and a second adsoriotn cycle from 0% RH to 90% RH. The equilibrium criterion was set to 99.0% step completion within a minimum of 60 minutes and a maximum of 5 hours for each increment. The weight change during the sorption cycle was monitored, allowing for the hygroscopic nature of the sample to be determined. The data collection interval was in seconds.

Thermogravimetric Differential Thermal Analysis (TG/DTA)

Thermogravimetric analyses were carried out on a Mettler Toledo TGA/DSC1 STARe. The calibration standards were indium and tin. Samples were placed in an aluminium sample pan, inserted into the TG furnace and accurately weighed. The heat flow signal was stabilised for one minute at 30° C., prior to heating to 270° C. in a stream of nitrogen at a rate of 10° C./minute.

Stability Tests

Approximately 25 mg of amorphous material and crystal form H obtained from example 1 was placed in separate vials (ca. 1.5 mL, open, clear glass vial). Three vials were placed into a beaker which was then stored in a sealed desiccator containing a sodium chloride solution which keeps a constant 75% RH. The desiccator was placed into an oven (oven brand: Swallow) at 40° C. One vial at a time was taken out after 7 days, 14 days and 1 month and analyzed. Ovens were temperature monitored using calibrated thermometers with min and max temperatures recorded throughout the stability study.

The following non-limiting examples are illustrative of the disclosure.

EXAMPLES

Comparative Example

Masitinib mesylate (25 mg) was charged into a scintillation vial followed by methanol (containing small amounts of water; 1.0 mL). The suspension was then heated until the masitinib mesylate had dissolved. The masitinib mesylate solution in methanol was then allowed to slowly cool to room temperature. The crystals which formed were then harvested by filtration and analyzed by XRPD and TG/DTA.

The obtained crystalline form of masitinib mesylate converted to masitinib mesylate crystal form I upon heating and lost small amounts of water, as detectable by TG/DTA, properties which fit the description of the hemihydrate DRX2 in the response to the ESR.

Preparatory Example

Approximately 250 mg of masitinib mesylate was dissolved in water (5 mL). The solution was filtered through a 0.2 µm PTFE filter into a clean vial. Aliquots of 0.5 mL were removed from the stock solution and placed into each of 10 vials. These were placed in a vial holder and the solutions frozen in a bath of liquid nitrogen. The frozen vials were placed inside a larger jar and placed on the freeze drier for approximately 24 hours. These were removed from the freeze drier and quickly capped to avoid moisture absorption from the atmosphere. XRPD analysis was performed on a sample of this material confirmed it to be X-ray amorphous.

Example 1

Amorphous masitinib mesylate obtained by freeze drying (125 mg, 99% purity) was charged into a scintillation vial and slurried in ethanol/water azeotrope (750 µl) for 7 days at room temperature prior to isolation by centrifugation and decantation. The obtained crystals were air dried and then analyzed by PLM, XRPD, DVS and TG/DTA. The crystals were found to be highly crystalline masitinib mesylate form H.

Example 2

Amorphous masitinib mesylate (125 mg, 99% purity) was charged into a scintillation vial and slurried in water-saturated dioxane (2.5 ml) for 7 days at room temperature prior to isolation by centrifugation and decantation. The obtained crystals were air dried and then used for analysis by PLM, XRPD, DVS and TG/DTA. The crystals were found to be highly crystalline masitinib mesylate form H.

Example 3

The polymorphic stability of masitinib mesylate form H as obtained from example 2 was assessed at 40° C./66% r.h.

After storage under those conditions for 7 days the XRPD pattern remained unchanged. Form H is thus stable at conditions of elevated temperature and humidity.

Example 4

The hygrosopicity of masitinib mesylate form H as obtained from example 2 was assessed by DVS. The DVS isotherm was initiated at 40% r.h. and increased to 70% r.h. The weight gain in this relative humidity interval was below 0.27% (w/w). Form H is thus less hygroscopic than masitinib mesylate form I.

What is claimed is:

1. A crystalline form of masitinib mesylate hydrate having an x-ray powder diffraction pattern comprising peaks at 2θ values of 7.8, 8.3, 10.9, 11.3, 24.0, and 33.2 measured at a temperature of about 20° C. and an x-ray wavelength (CuKα), λ, of 1.5418 Å.

2. The crystalline form according to claim 1, further comprising peaks at 2θ values of 11.0, 17.4, and 28.0 measured at a temperature of about 20° C. and an x-ray wavelength (CuKα), λ, of 1.5418 Å.

3. The crystalline form according to claim 1, further including from 2.0% to 7.0% of water (w/w).

4. The crystalline form according to claim 1 in substantially pure form.

5. The crystalline form according to claim 1, further including less than 10% by weight of masitinib mesylate crystal form I, wherein form I having an x-ray powder diffraction pattern (XRPD) comprising peaks at 2θ values of 11.04, 14.48, 16.72, 18.22 and 19.25, measured at a temperature of about 20° C. and an x-ray wavelength (CuKα), λ, of 1.5418 Å.

6. The crystalline form according to claim 1, further including less than 5% by weight of masitinib mesylate crystal form I, wherein form I having an x-ray powder diffraction pattern (XRPD) comprising peaks at 2θ values of 11.04, 14.48, 16.72, 18.22 and 19.25, measured at a temperature of about 20° C. and an x-ray wavelength (CuKα), λ, of 1.5418 Å.

7. The crystalline form according to claim 1, further including less than 3% by weight of masitinib mesylate crystal form I, wherein form I having an x-ray powder diffraction pattern (XRPD) comprising peaks at 2θ values of 11.04, 14.48, 16.72, 18.22 and 19.25, measured at a temperature of about 20° C. and an x-ray wavelength (CuKα), λ, of 1.5418 Å.

8. The crystalline form according to claim 1, further including less than 1% by weight of masitinib mesylate crystal form I, wherein form I having an x-ray powder diffraction pattern (XRPD) comprising peaks at 2θ values of 11.04, 14.48, 16.72, 18.22 and 19.25, measured at a temperature of about 20° C. and an x-ray wavelength (CuKα), λ, of 1.5418 Å.

9. A pharmaceutical composition comprising the crystalline form of claim 1 and a pharmaceutically acceptable carrier or diluent.

10. A composition comprising the crystalline form of masitinib mesylate hydrate according to claim 1, wherein the aspect ratio of the masitinib mesylate hydrate crystals is from 1 to 3.

* * * * *